(12) United States Patent
Ayturk et al.

(10) Patent No.: US 10,183,108 B2
(45) Date of Patent: Jan. 22, 2019

(54) INLINE DIAFILTRATION WITH MULTI-CHANNEL PUMP

(71) Applicant: Pall Corporation, Port Washington, NY (US)

(72) Inventors: Engin Ayturk, Shrewsbury, MA (US); Catherine Casey, Framingham, MA (US)

(73) Assignee: Pall Corporation, Port Washington, NY (US)

( * ) Notice: Subject to any disclaimer, the term of this patent is extended or adjusted under 35 U.S.C. 154(b) by 409 days.

(21) Appl. No.: 15/015,350

(22) Filed: Feb. 4, 2016

(65) Prior Publication Data
US 2017/0225123 A1  Aug. 10, 2017

(51) Int. Cl.
*A61M 1/34* (2006.01)
*B01D 61/14* (2006.01)
(Continued)

(52) U.S. Cl.
CPC ........... *A61M 1/3413* (2013.01); *B01D 61/14* (2013.01); *B01D 61/145* (2013.01); *B01D 61/18* (2013.01);
(Continued)

(58) Field of Classification Search
CPC .......... B01D 2311/165; B01D 2313/18; B01D 2313/243; B01D 2315/10; B01D 2315/16;
(Continued)

(56) References Cited

U.S. PATENT DOCUMENTS

| 5,616,595 A | 4/1997 | Chu et al. |
| 6,139,746 A | 10/2000 | Kopf |

(Continued)

FOREIGN PATENT DOCUMENTS

| CN | 2600159 Y | 1/2004 |
| JP | H11-169671 A | 6/1999 |

(Continued)

OTHER PUBLICATIONS

European Patent Office, European Search Report in counterpart European Application No. 17 15 1017, dated Jun. 27, 2017.
(Continued)

*Primary Examiner* — John Kim
(74) *Attorney, Agent, or Firm* — Leydig Voit & Mayer

(57) ABSTRACT

A diafiltration system comprises a fluid treatment assembly comprising two or more fluid treatment modules, the fluid treatment assembly comprising a feed inlet, a permeate outlet, and a retentate outlet; each module comprising a cross flow treatment assembly including an ultrafiltration membrane and having a feed side and a permeate side, and a diafiltration fluid distribution plate comprising a diafiltration fluid feed inlet and a common feed permeate/diafiltration fluid permeate outlet port; two or more diafiltration fluid conduits, each conduit in fluid communication with a respective single diafiltration fluid feed inlet; and, a diafiltration fluid pump comprising at least a first multiple channel pump head having at least two channels including separate channels for separate conduits in fluid communication with respective single diafiltration fluid feed inlets, wherein the pump provides simultaneously controlled diafiltration fluid flow rates through each of the conduits to the respective diafiltration fluid feed inlets.

6 Claims, 10 Drawing Sheets

(51) Int. Cl.
  *B01D 61/22* (2006.01)
  *B01D 61/18* (2006.01)
  *B01D 63/08* (2006.01)
  *C07K 1/34* (2006.01)
  *C07K 16/00* (2006.01)

(52) U.S. Cl.
  CPC ............ *B01D 61/22* (2013.01); *B01D 63/08* (2013.01); *B01D 63/085* (2013.01); *C07K 1/34* (2013.01); *C07K 16/00* (2013.01); *B01D 2311/16* (2013.01); *B01D 2311/165* (2013.01); *B01D 2313/18* (2013.01); *B01D 2313/243* (2013.01); *B01D 2313/54* (2013.01); *B01D 2315/10* (2013.01); *B01D 2315/16* (2013.01); *B01D 2319/04* (2013.01)

(58) Field of Classification Search
  CPC .............. B01D 61/145; B01D 2311/16; B01D 2313/54; B01D 2319/04; B01D 61/14; B01D 61/18; B01D 61/22; B01D 63/08; B01D 63/085; C07K 16/00; C07K 1/34; A61M 1/3413; A61M 1/3417
  See application file for complete search history.

(56) References Cited

U.S. PATENT DOCUMENTS

| | | | |
|---|---|---|---|
| 7,918,999 | B2 | 4/2011 | Gagnon et al. |
| 8,980,088 | B2 | 3/2015 | Forman et al. |
| 2002/0043487 | A1 | 4/2002 | Schick |
| 2007/0244306 | A1 | 10/2007 | Tanahashi et al. |
| 2008/0135499 | A1 | 6/2008 | Gagnon et al. |
| 2008/0277343 | A1 | 11/2008 | Schick |
| 2012/0168368 | A1 | 7/2012 | De Los Reyes et al. |
| 2013/0037486 | A1 | 2/2013 | Sayer et al. |
| 2013/0118971 | A1 | 5/2013 | Sayer et al. |
| 2014/0042072 | A1 | 2/2014 | Sayer et al. |
| 2015/0111252 | A1 | 4/2015 | Hirschel et al. |
| 2015/0360180 | A1 | 12/2015 | Lutz et al. |
| 2015/0375173 | A1 | 12/2015 | Steen |
| 2016/0059159 | A1 | 3/2016 | Steen et al. |
| 2016/0059160 | A1 | 3/2016 | Steen et al. |

FOREIGN PATENT DOCUMENTS

| | | |
|---|---|---|
| JP | 2003-512594 A | 4/2003 |
| JP | 2011-6466 A | 1/2011 |
| WO | WO 2010/107677 A1 | 9/2010 |
| WO | WO 2015/010097 A2 | 1/2015 |

OTHER PUBLICATIONS

Japanese Patent Office, Office Action in counterpart Japanese Application No. 2017-003672, dated Feb. 27, 2018.

Intellectual Property Office of Singapore, Singapore Search Report in counterpart Singapore Application No. 10201700425W, dated Aug. 21, 2017.

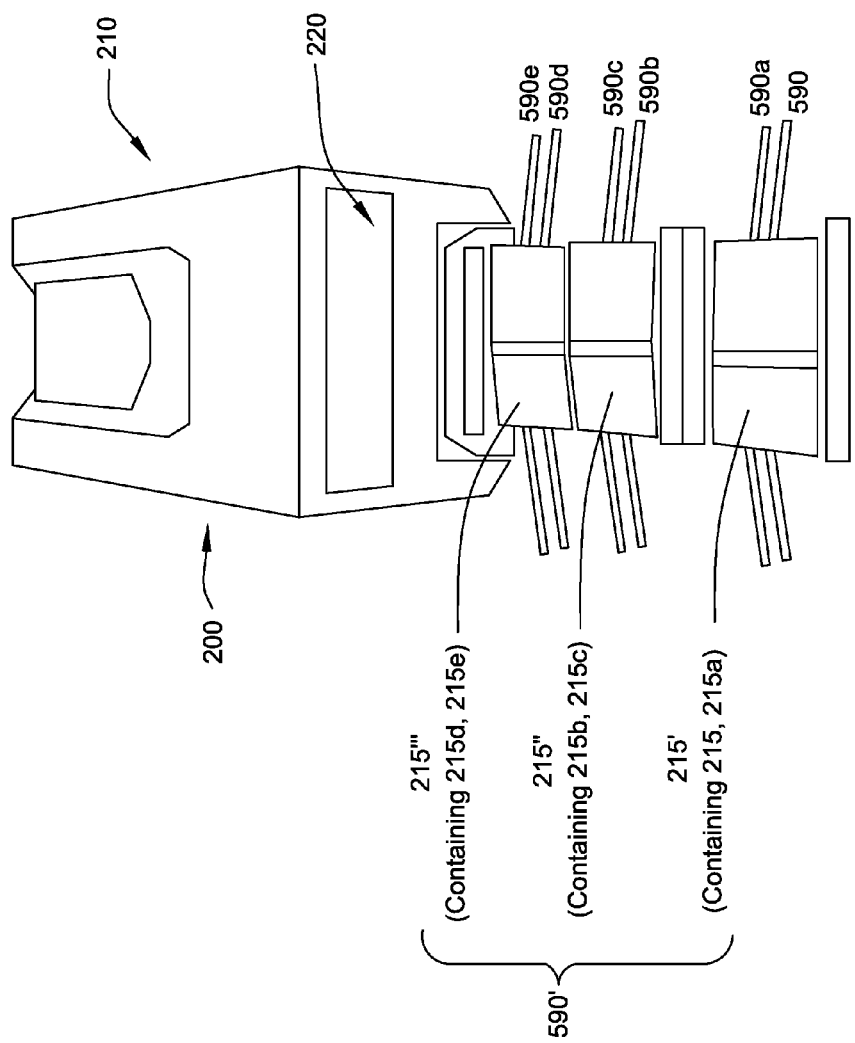

INLINE DIAFILTRATION WITH MULTI-CHANNEL PUMP

BACKGROUND OF THE INVENTION

Diafiltration is a technique that uses ultrafiltration (UF) membranes to remove, replace, or lower the concentration of undesirable materials such as salts and/or solvents from fluids containing desirable materials, for example, desired biomolecules such as proteins, peptides, and nucleic acids. A UF membrane retains molecules that are larger than the pores of the membrane (the solution containing the retained molecules is referred to as the retentate or concentrate), and smaller molecules such as salts, solvents, and water (which are 100% permeable), freely pass through the membrane (providing a solution referred to as the permeate or filtrate).

Continuous diafiltration (sometimes referred to as constant volume diafiltration) involves washing out the original buffer salts (and/or other low molecular weight species) in the retentate by adding water or new buffer to the retentate at the same rate as filtrate is being generated. As a result, the retentate volume and product concentration does not change during the diafiltration process. If water is used for diafiltering, the salts will be washed out and the conductivity lowered. If a buffer is used for diafiltering, the new buffer salt concentration will increase at a rate inversely proportional to that of the species being removed, and the conductivity will be increased. The amount of salt removed is related to the filtrate volume generated, relative to the retentate volume. The filtrate volume generated is usually referred to in terms of "diafiltration volumes." A single diafiltration volume (DV) is the volume of retentate when diafiltration is started. For continuous diafiltration, liquid is added at the same rate as filtrate is generated. When the volume of filtrate collected equals the starting retentate volume, 1 DV has been processed. Using continuous diafiltration, greater than 99.5% of a 100% permeable solute can be removed by washing through 6 retentate volumes (6 DV) with the buffer of choice.

However, there is a need for improved diafiltration systems and methods.

The present invention provides for ameliorating at least some of the disadvantages of the prior art. These and other advantages of the present invention will be apparent from the description as set forth below.

BRIEF SUMMARY OF THE INVENTION

An embodiment of the invention provides a diafiltration system comprising (a) a fluid treatment assembly comprising two or more fluid treatment modules, the fluid treatment assembly comprising a feed inlet, and permeate outlet, and a retentate outlet; (i) each fluid treatment module comprising a cross flow treatment assembly including at least one ultrafiltration membrane, the fluid treatment assembly comprising having at least one feed side and at least one opposite permeate side, and a diafiltration fluid distribution plate comprising a diafiltration fluid feed inlet and a common feed permeate/diafiltration fluid permeate outlet port; (b) two or more separate diafiltration fluid conduits, each separate diafiltration fluid conduit in fluid communication with a respective single diafiltration fluid feed inlet; and, (c) a diafiltration fluid pump, the diafiltration fluid pump comprising at least a first multiple channel pump head having at least two channels including separate channels for separate diafiltration fluid conduits in fluid communication with respective single diafiltration fluid feed inlets, wherein the diafiltration pump provides simultaneously controlled diafiltration fluid flow rates through each of the separate diafiltration fluid conduits to the respective single diafiltration fluid feed inlets.

In another embodiment, a method of diafiltration is provided, the method comprising passing a feed fluid containing undesirable material and desirable biomolecules, and a diafiltration fluid suitable for washing out undesirable material from the feed fluid, through the fluid treatment assembly in an embodiment of the diafiltration system, wherein the method includes (a) passing the feed fluid at a controlled feed fluid flow rate through the feed inlet of the fluid treatment assembly; (b) passing the diafiltration fluid at a controlled diafiltration fluid flow rate through each of the separate diafiltration fluid conduits in fluid communication with respective single diafiltration fluid feed inlets, such that the diafiltration fluid washes undesirable material from the feed fluid, wherein the controlled diafiltration fluid flow rate is simultaneously controlled through each of the separate diafiltration fluid conduits; (c) passing a feed permeate/diafiltration fluid permeate fluid through each of the common feed permeate/diafiltration fluid permeate outlet ports; (d) passing a retentate fluid from the retentate outlet of fluid treatment assembly, the retentate fluid comprising desirable biomolecules and a lower concentration of undesirable material than the concentration of undesirable material in the feed fluid; and (e) passing the feed permeate/diafiltration fluid permeate fluid from the permeate outlet of the fluid treatment assembly.

BRIEF DESCRIPTION OF THE SEVERAL VIEWS OF THE DRAWING(S)

FIG. 1A is a diagrammatic view of a diafiltration pump including a plurality of multiple channel pump heads for use in an embodiment of the invention.

FIG. 2B shows individual components, and FIG. 2C shows some of the components combined to show sub-assemblies.

Figure 3A:
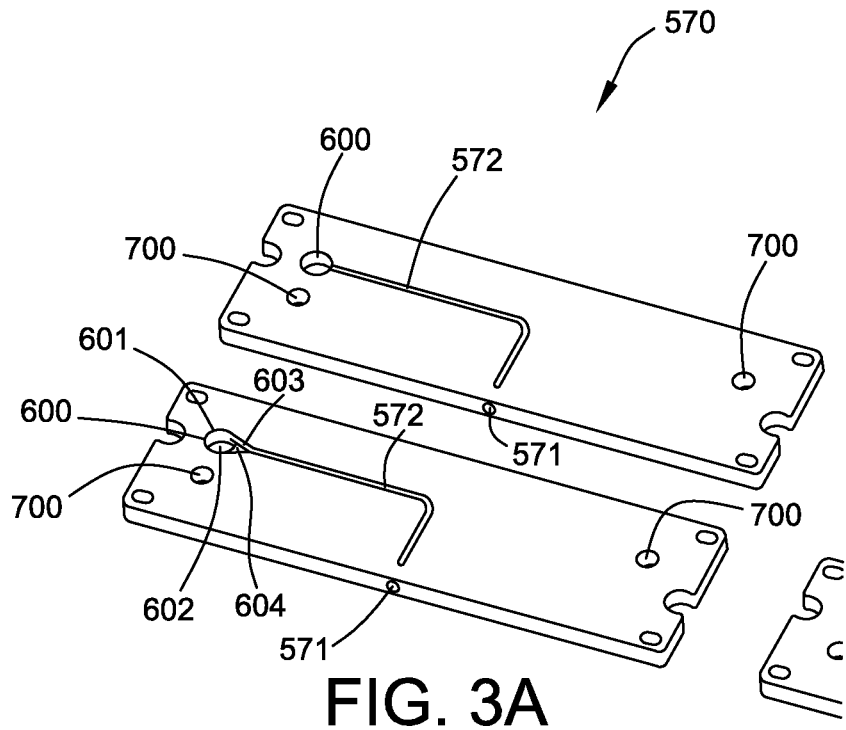
Figure 3B:
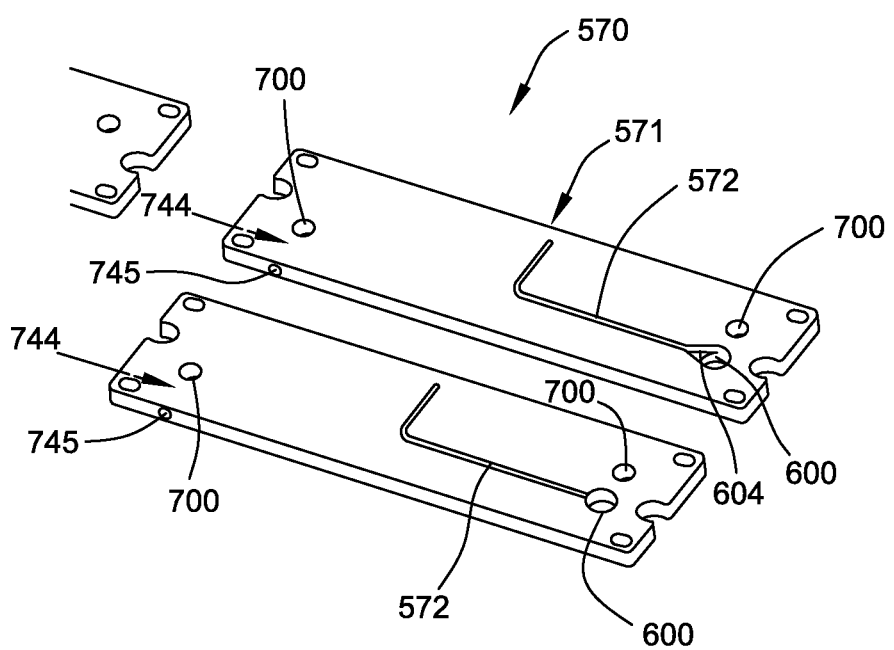
Figure 4A:
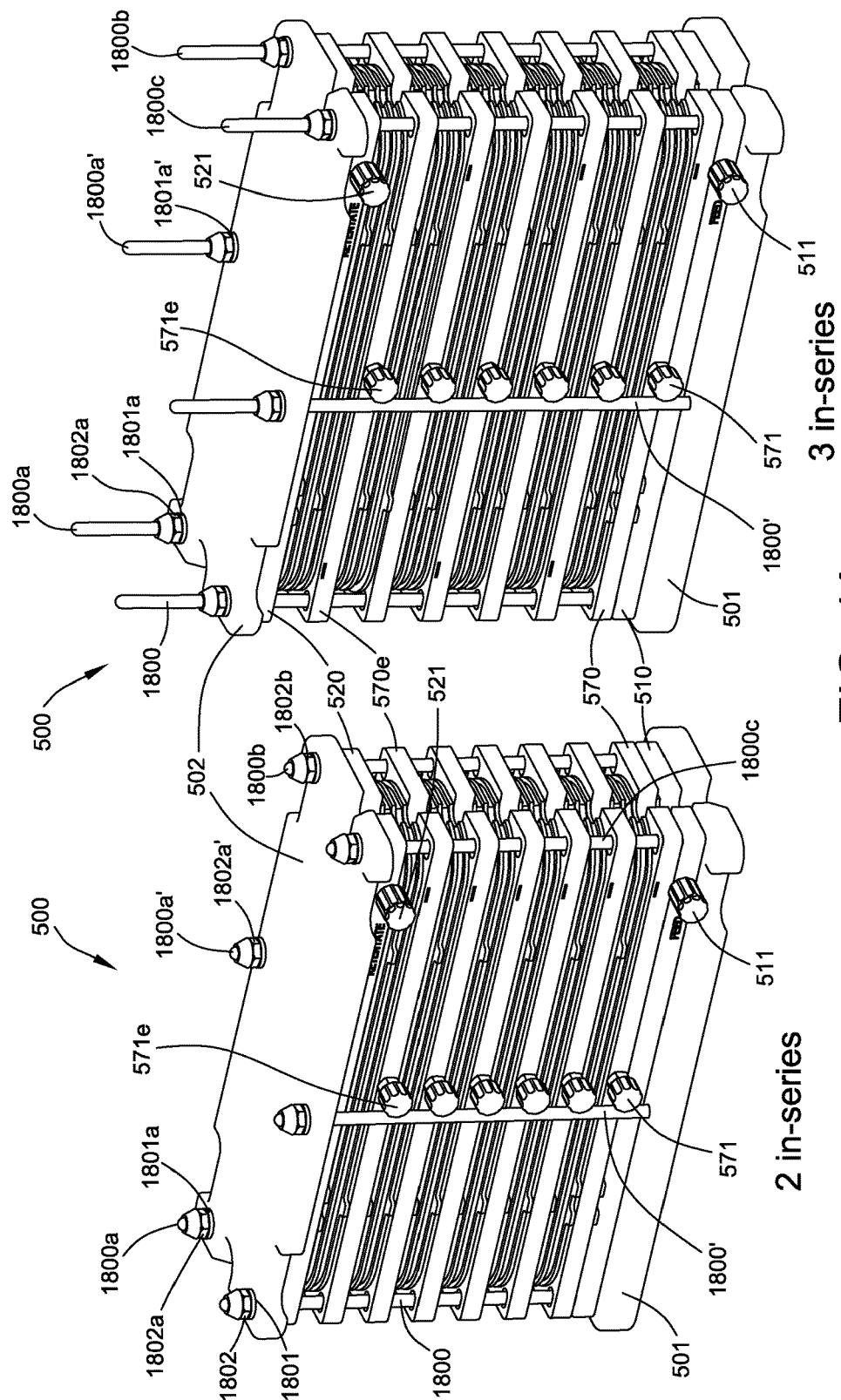
Figure 4B:
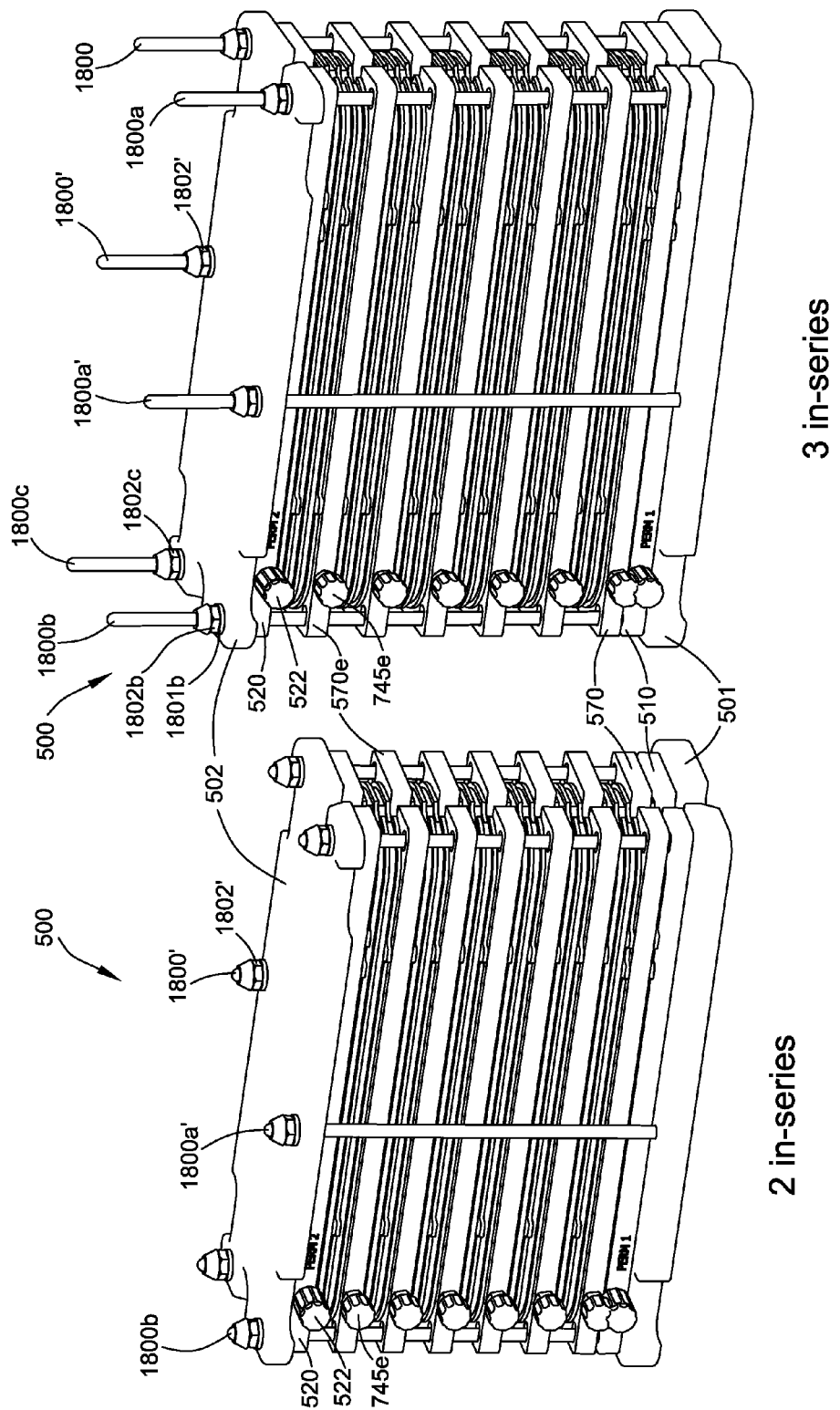
Figure 4C:
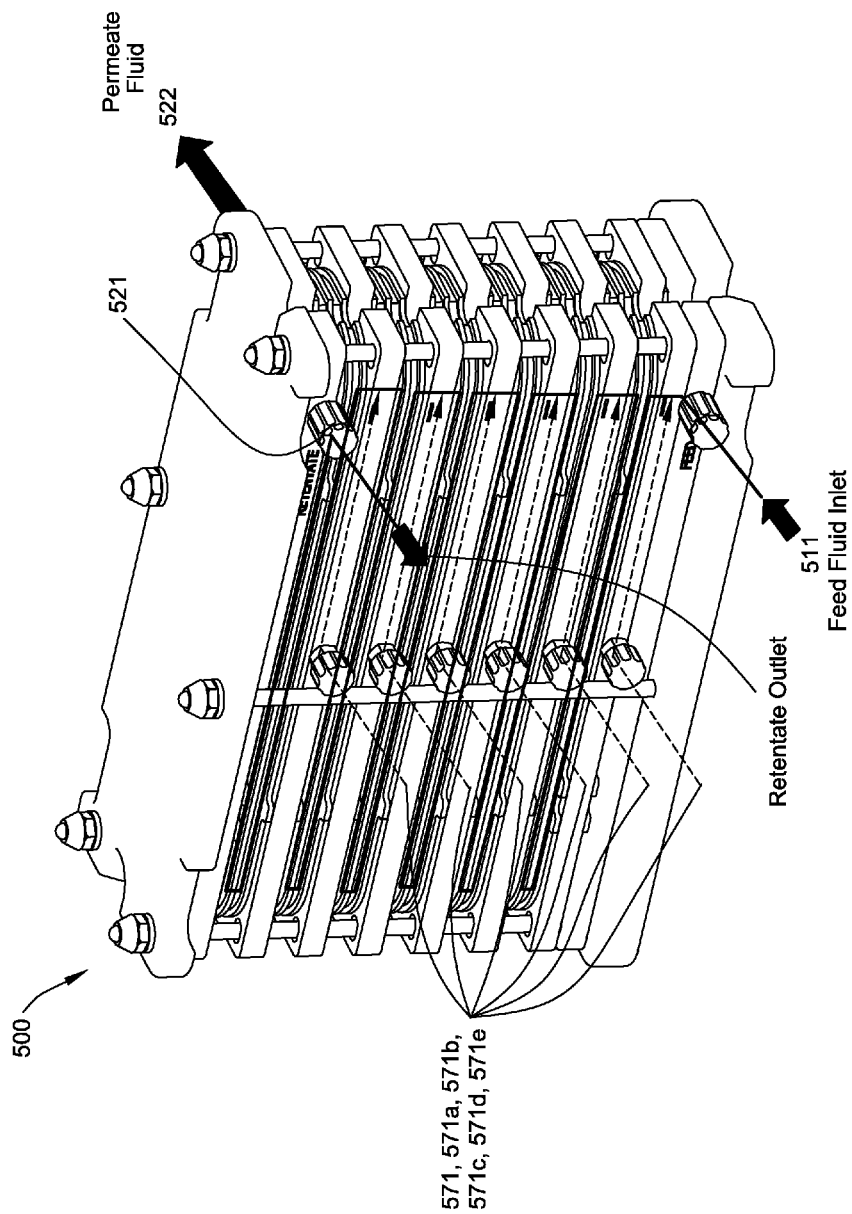

FIG. 3A and FIG. 3B show top perspective views of exemplary diafiltration fluid distribution plates for use in fluid treatment modules, the plates each including a diafiltration fluid feed inlet, a diafiltration fluid inlet port, a diafiltration fluid feed channel, a diafiltration fluid permeate port, and a diafiltration fluid permeate outlet FIG. 4A is a front view of 2 assembled fluid treatment assemblies including 6 fluid treatment modules, one set of modules including 2 in-series cross flow treatment assemblies, the other set of modules including 3 in-series cross flow treatment assemblies; FIG. 4B is a rear view of the assembled fluid treatment assemblies shown in FIG. 4A, and FIG. 4C shows fluid flow pathways through the fluid treatment assembly including 2 in-series cross flow treatment assemblies shown in FIG. 4A.

DETAILED DESCRIPTION OF THE INVENTION

In accordance with an embodiment of the present invention, a diafiltration system is provided, the system comprising (a) a fluid treatment assembly comprising two or more fluid treatment modules, the fluid treatment assembly comprising a feed inlet, and permeate outlet, and a retentate outlet; (i) each fluid treatment module comprising a cross flow treatment assembly including at least one ultrafiltration membrane, the cross flow treatment assembly having at least one feed side and at least one opposite permeate side, and a diafiltration fluid distribution plate comprising a diafiltration fluid feed inlet and a common feed permeate/diafiltration fluid permeate outlet port; (b) two or more separate diafiltration fluid conduits, each separate diafiltration fluid conduit in fluid communication with a respective single diafiltration fluid feed inlet; and, (c) a diafiltration fluid pump, the diafiltration fluid pump comprising at least a first multiple channel pump head having at least two channels including separate channels for separate diafiltration fluid conduits in fluid communication with respective single diafiltration fluid feed inlets, wherein the diafiltration pump provides simultaneously controlled diafiltration fluid flow rates through each of the separate diafiltration fluid conduits to the respective single diafiltration fluid feed inlets.

In another embodiment, a diafiltration fluid distribution plate is provided, the plate comprising a diafiltration fluid feed inlet and the diafiltration fluid feed channel communicating with the diafiltration fluid feed inlet, and a common feed retentate port, wherein the common feed retentate port has 2 different inner diameters.

Typically, the diafiltration system further comprises a feed fluid pump and a feed fluid conduit, wherein the feed fluid conduit is in fluid communication with the fluid treatment assembly feed inlet, wherein the feed fluid pump provides a controlled feed fluid flow rate through the feed fluid conduit to the fluid treatment assembly feed inlet.

In an embodiment, the diafiltration system includes at least one additional channel pump head having including a separate channel for a separate diafiltration fluid conduit in fluid communication with a single diafiltration fluid feed inlet, wherein the pump, via the first multiple channel pump head and the additional channel pump head, provides simultaneously controlled diafiltration fluid flow rates through each of the separate diafiltration fluid conduits to the respective single diafiltration fluid feed inlets.

Alternatively, or additionally, an embodiment of the diafiltration system of claim includes at least one additional multiple channel pump head having at least two channels including a separate channel for a separate diafiltration fluid conduit in fluid communication with a single diafiltration fluid feed inlet, wherein the pump, via the first multiple channel pump head and the additional multiple channel pump head, provides simultaneously controlled diafiltration fluid flow rates through each of the separate diafiltration fluid conduits to the respective single diafiltration fluid feed inlets.

In some embodiments, the diafiltration system further comprises a retentate throttling valve, arranged to allow the system to maintain a desired ratio of feed flow rate to retentate flow rate.

In another embodiment, a method of diafiltration is provided, the method comprising passing a feed fluid containing undesirable material and desirable biomolecules, and a diafiltration fluid suitable for washing out undesirable material from the feed fluid, through the fluid treatment assembly in an embodiment of the diafiltration system, wherein the method includes (a) passing the feed fluid at a controlled feed fluid flow rate through the feed inlet of the fluid treatment assembly; (b) passing the diafiltration fluid at a controlled diafiltration fluid flow rate through each of the separate diafiltration fluid conduits in fluid communication with respective single diafiltration fluid feed inlets, such that the diafiltration fluid washes undesirable material from the feed fluid, wherein the controlled diafiltration fluid flow rate is simultaneously controlled through each of the separate diafiltration fluid conduits; (c) passing a feed permeate/diafiltration fluid permeate fluid through each of the common feed permeate/diafiltration fluid permeate outlet ports; (d) passing a retentate fluid from the retentate outlet of fluid treatment assembly, the retentate fluid comprising desirable biomolecules and a lower concentration of undesirable material than the concentration of undesirable material in the feed fluid; and (e) passing the feed permeate/diafiltration fluid permeate fluid from the permeate outlet of the fluid treatment assembly.

Typically, e.g., for some applications wherein at least 2 log (99%) removal efficiencies are desirable, the feed fluid pump provides a controlled feed fluid flow rate through the feed fluid conduit to the fluid treatment assembly feed inlet at a flow rate that is lower than (e.g., at least about 10% lower than) the simultaneously controlled diafiltration fluid flow rates through each of the separate diafiltration fluid conduits provided by the diafiltration pump.

The invention is suitable for discontinuous diafiltration (including sequential dilution and volume reduction), and, more preferably, continuous diafiltration, wherein the diafiltration fluid flow rate is managed through a single point of control. Additionally, while "continuous diafiltration" as conventionally carried out involves the continuous addition of buffer to into the product tank, and the product of interest (e.g., desirable proteins) is recirculated within the system, embodiments of the invention can encompass "continuous diafiltration in its entirety," such that the product of interest is not recirculated within the system; rather, it is processed continuously in a single-pass mode of operation.

Fluids can be passed through the fluid treatment assembly in co-current and counter-current flow directions, in a single-pass mode or a continuous-pass mode.

Fluid treatment assemblies can include any number of fluid treatment modules (e.g., "stages," such as 2, 3, 4, 5, 6, 7, or more, stages), wherein an individual module (stage) includes one or more cross fluid treatment assemblies). Fluid treatment assemblies (including feed and/or permeate channels) can be arranged in any flow configuration (serial flow and/or parallel flow) to provide a fluid path of desired length (e.g., 1-in-series, 2-in-series, etc.). In-line diafiltration is preferred.

Advantages include one or more of any of the following: a reduced footprint, a reduced number of moving parts, improved process integration including simplified operational requirements, reduced working volume, and reduced hold up volume.

A variety of desired removal efficiencies can be obtained, e.g., about 99% (2 log), about 99.9% (3 log) and about 99.99% (4 log), or even higher. However, for some applications, lower buffer efficiencies are suitable.

As noted above, typically, the feed fluid pump provides a controlled feed fluid flow rate through the feed fluid conduit to the fluid treatment assembly feed inlet at a flow rate that is lower than the simultaneously controlled diafiltration fluid flow rates through each of the separate diafiltration fluid conduits provided by the diafiltration pump (i.e., the diafiltration fluid rate through each channel is higher than the feed fluid flow rate). Illustratively, in one embodiment of the system comprising a fluid treatment assembly including 6 stages, operated co-currently, the controlled diafiltration fluid flow rates through each of the separate diafiltration fluid conduits is at least about 13% higher, providing a 2 log removal efficiency; at least about 50% higher, providing a 3 log removal efficiency; and at least about 70% higher, providing a 4 log removal efficiency.

Each of the components of the invention will now be described in more detail below, wherein like components have like reference numbers.

Figure 1B:
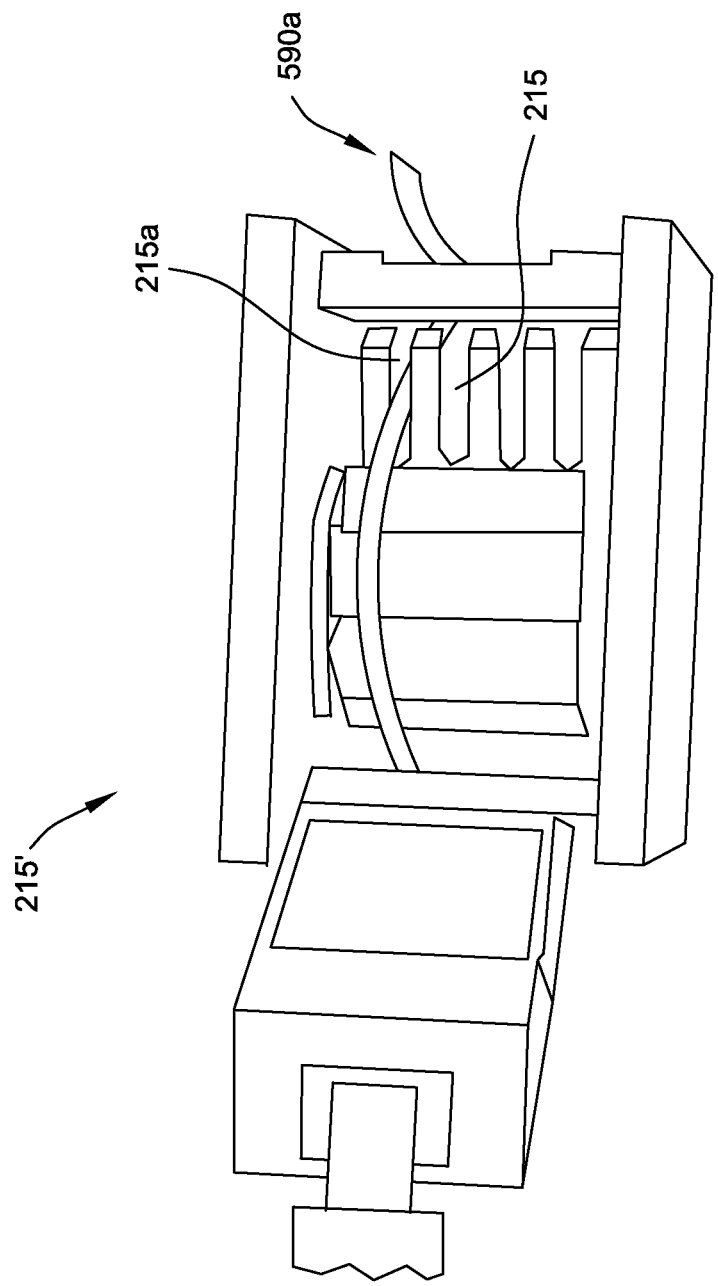
FIG. 1B is a diagrammatic view of an open multiple channel pump head, illustrating separate channels.

FIG. 1A shows an illustrative embodiment of a diafiltration system 1000, comprising a diafiltration pump 200 including a driver 210 (preferably microprocessor controlled), multiple channel pump heads 215' (including separate channels 215 and 215a), 215'' (including separate channels 215b and 215c), and 215''' (including separate channels 215d and 215e) (215' with separate channels 215, 215a, shown in more detail in FIG. 1B), wherein the channels are suitable for receiving conduits such as diafiltration fluid conduits, wherein the system also includes a fluid treatment assembly 500. Typically, the diafiltration pump also includes a display 220.

The illustrative fluid treatment assembly 500 shown in FIGS. 2A-2D, and 4A-4C comprises a bottom support plate 501, a top support plate 502, a bottom manifold plate 510 (e.g., a feed bottom manifold plate), and a top manifold plate 520 (e.g., a retentate/permeate top manifold plate), wherein the bottom and top manifold plates include one or more ports, such as a feed inlet 511, a retentate outlet 521, and a permeate outlet 522. In the fluid treatment assembly 500 shown in FIGS. 4A and 4B, the bottom manifold plate 510 comprises the feed inlet 511 (for introducing feed solution into the filter assembly), and the top manifold plate comprises the retentate outlet 521 (which allows buffer exchanged feed (e.g., protein) solution to pass to a collection vessel) and the permeate outlet 522 (which discharges exchange buffer).

Figure 2A:
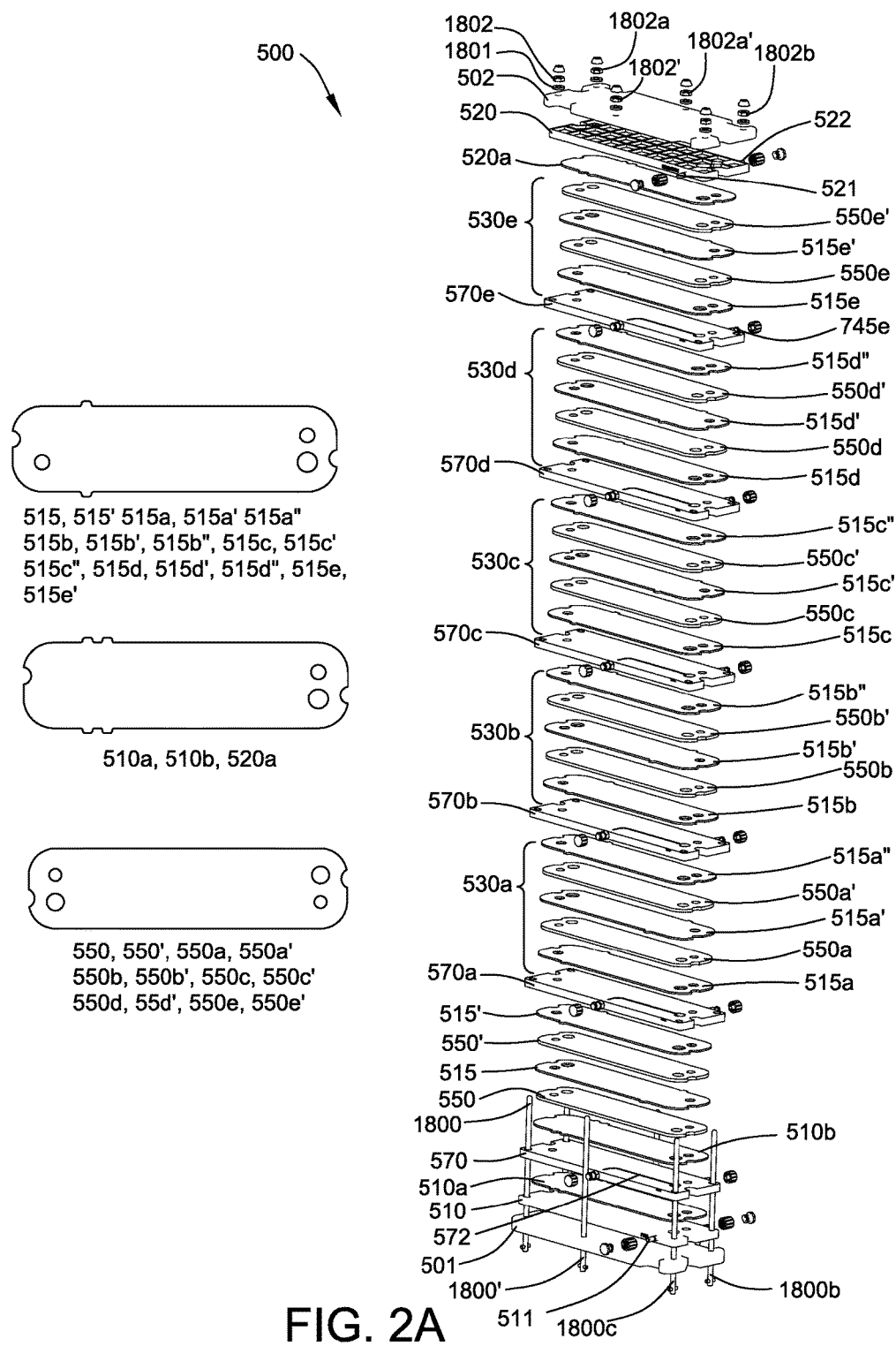
FIG. 2A is an exploded view of an illustrative fluid treatment assembly including a plurality of fluid treatment modules, the fluid treatment modules including cross flow treatment assemblies.
Figures 2B, 2C:
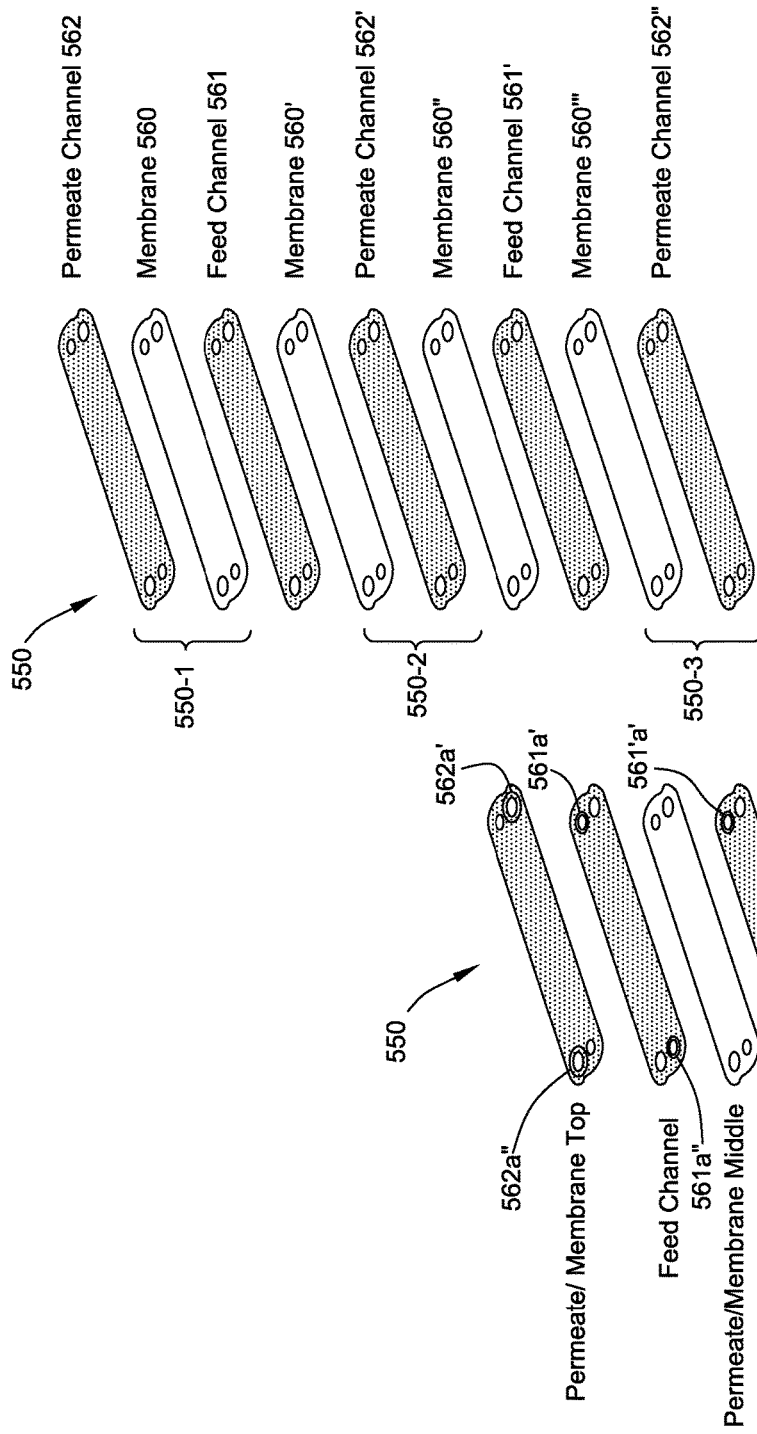
FIGS. 2B and 2C show exploded views of a cross flow treatment assembly in a fluid treatment module shown in FIG. 2A.

As shown in, for example, FIG. 2A, the fluid treatment assembly 500 includes two or more fluid treatment modules 530, (530a, 530b, 530c, 530d, 530e). While a fluid treatment module can include a single cross flow treatment assembly, typically, and as illustrated in FIG. 2A for example, an individual treatment module includes a plurality of cross flow treatment assemblies (550, 550', 550a, 550a', 550b, 550b', 550c, 550c', 550d, 550d', 550e, 550e'), each including at least one ultrafiltration membrane (membranes are shown in FIG. 2B, illustrating membranes 560, 560', 560" and 560''' in a single cross flow treatment assembly), the cross flow treatment assembly having at least one feed side (sometimes referred to as a feed channel or feed layer) (illustratively shown in FIG. 2B, showing feed channels 561, 561'), and at least one opposite permeate side (sometimes referred to as a permeate channel or permeate layer) (illustratively shown in FIG. 2B, showing permeate channels 562, 562', 562''), and (as shown particularly in FIGS. 3A and 3B) a diafiltration distribution plate 570 (570a, 570b, 570c, 570d, 570e) comprising a diafiltration fluid feed inlet 571 (571a, 571b, 571c, 571d, 571e), a diafiltration fluid feed channel 572 (572a, 572b, 572c, 572c, 572e) in fluid communication with the diafiltration fluid feed inlet 571 and a common feed/retentate port 600 (600a, 600b, 600c, 600d, 600e), and at least one (2 are illustrated in each plate) common feed permeate/diafiltration fluid permeate outlet port 700 (700a, 700b, 700c, 700d, 700e).

If desired, the diafiltration plate can include a common feed permeate/diafiltration fluid permeate outlet channel 744 (744a, 744b, 744c, 744d, 744e) and a common feed permeate/diafiltration fluid permeate aperture 745 (745a, 745b, 745c, 745d, 745e) in fluid communication with the common feed permeate/diafiltration fluid permeate outlet port. In some applications, some or all of the apertures are capped, preventing fluid flow therethrough (such that fluid flows through the common feed permeate/diafiltration fluid permeate outlet port 700, but not the common feed permeate/diafiltration fluid permeate outlet channel 744 or the common feed permeate/diafiltration fluid permeate aperture 745).

FIGS. 3A and 3B also various configurations for the common feed/retentate port and the diafiltration fluid feed channel in the diafiltration plate, for introducing the diafiltration fluid into the feed/retentate port at different angles. In one embodiment, the "teardrop shaped" port 600 has 2 different inner diameters (601 having a larger opening coming to a point 603 at one surface of the plate, the opening being larger than the opening 602 in the round port below, such that there is a lip or shoulder 604 between the teardrop shape and the round aperture) may provide improved results, e.g., by providing a larger surface area for the mixing of feed and diafiltration (buffer) fluid streams.

Typically, the fluid treatment assembly includes at least one, more preferably, at least two, gaskets, wherein at least one gasket has 3 apertures and at least one gasket has 2 apertures. For example, FIG. 2A illustrates gasket 510a between the first stage 530 and lower manifold plate 510, gasket 520b between sixth stage 530e and the upper manifold plate 520, and gasket 510b between diafiltration plate 570 and cross treatment assembly 550, wherein each gasket has 2 apertures, and FIG. 2A also illustrates gaskets 515 (515', 515a, 515a', 515a'', 515b, 515b', 515b'', 515c, 515c', 515c'', 515d, 515d', 515d'', 515e, 515e') each having 3 apertures, on either side of the cross flow assemblies, with the exception of the first and last cross flow assemblies (wherein gaskets 510b and 520a are on one side of the cross flow treatment assemblies). In a (non-illustrated) variation of the embodiment shown in FIG. 2A, cross flow treatment assembly 530 is replaced by a second manifold plate 510.

The illustrated system 1000 includes a plurality of separate diafiltration fluid feed conduits 590' (590, 590a, 590b, 590c, 590d, 590e), in fluid communication with a diafiltration fluid (e.g., buffer fluid) source 1570, and diafiltration fluid feed inlets, wherein the diafiltration fluid feed conduits are separately arranged in the separate channels of the multiple channel pump head(s). Accordingly, while individual diafiltration fluid feed conduit can be in fluid communication with a common diafiltration fluid source, an individual diafiltration fluid feed conduit only communicates with a single respective diafiltration feed fluid inlet of an individual cross flow treatment assembly, and the fluid flow rate through the individual conduit is controlled.

The fluid treatment assembly can be assembled as is known in the art. In the illustrated assembly shown in FIGS. 4A and 4B, the modules are stacked. If desired, the fluid treatment assemblies can include, for example, rods (e.g., compression and/or mounting rods), bolts, nuts, and washers, including, for example, as disclosed in U.S. Pat. No. 7,918,999, and U.S. Patent Application Publications 2008/

0135499 and 2013/0118971. In the illustrated embodiments, the fluid treatment assemblies include threaded compression rods 1800 (1800a, 1800b, 1800c), threaded mounting rods 1800', 1800a' (wherein the mounting rods only pass through the support plates, and the compression rods pass through the support plates, the manifold plates and the diafiltration plates), washers 1801 (1801a, 1801b, 1801c; 1801', 1800a') and threaded nuts 1802 (1802a, 1802b, 1802c; 1802', 1802a'), wherein the top and bottom support plates, the top and bottom manifold plates, and the diafiltration distribution plates, include holes allowing the rods to pass therethrough such that the modules can be stacked. Typically, the mounting rods provide alignment support during stacking and assembling the modules, and the compression rods ensure application of a desired load and torque to functionalize the fluid treatment assembly.

Other assembly configurations are known in the art, e.g., including bands or holderless configurations, for example, as disclosed in U.S. Patent Application Publication 2013/0118971.

Figure 2D:
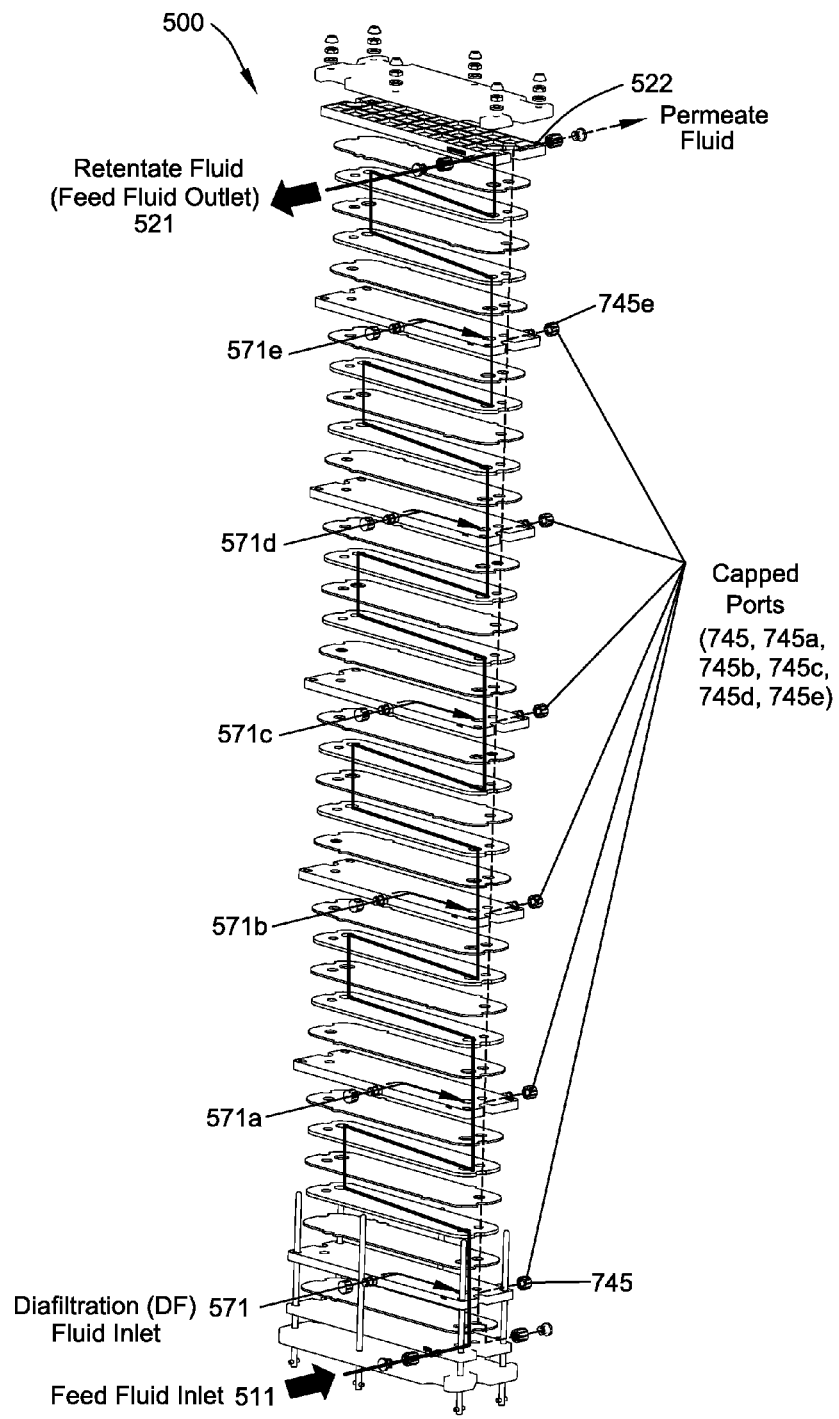
FIG. 2D shows fluid flow pathways through the fluid treatment assembly shown in FIG. 2A.

Typically, the system 1000 further comprises a feed fluid pump 1500, a feed fluid source 1510, and at least one feed fluid conduit, 1511, in fluid communication with the feed inlet 511, at least one retentate conduit 1521 in fluid communication with the retentate outlet 521 and a collection container 1621, at least one permeate conduit 1522 in fluid communication with the permeate outlet 522 and a permeate/waste container 1622, typically, wherein the permeate conduit 1522 is also in fluid communication with one or more common feed permeate/diafiltration fluid permeate outlet ports (e.g., FIG. 2D shows permeate passing through each of the common permeate ports (700, 700a, 700b, 700c, 700d, 700e) through permeate outlet 522 to permeate conduit 1522).

Additionally, or alternatively, if desired (e.g., for some applications involving counter-current operation), the system can include one or more diafiltration fluid permeate conduits in fluid communication with the common feed permeate/diafiltration fluid permeate outlet channels 744 (744, 744a, 744b) and the common feed permeate/diafiltration fluid permeate apertures (745, 745a, 745b (the apertures shown as capped in FIG. 2D)) and the permeate/waste container 1622 and/or a diafiltration permeate container (conduits and diafiltration permeate container not shown).

The system can also include, for example, one or more monitoring devices for monitoring one or more of any of the following: pressure (e.g., inlet pressure, outlet pressure and/or backpressure), flow rates, and conductivity, and/or one or more valves, e.g., retentate and/or permeate throttling valves (sometimes referred to as control valves), for example, for adjusting one or more of any of the following: flow ratio between feed and retentate, and/or adjusting backpressure. Suitable flow meters, pressure sensors, conductivity sensors, and throttle valves are known in the art.

In some embodiments, the system comprises flow meters and pressure sensors associated with each inlet fluid flow path communicating with the fluid treatment assembly, and with the retentate fluid path exiting the fluid treatment assembly, and conductivity sensors and throttle valves associated with the retentate and permeate fluid flow paths exiting the fluid treatment assembly. Typically, a flow meter and a pressure sensor are associated with the feed fluid inlet fluid flow path, and a flow meter and a pressure sensor is associated with the retentate fluid flow path.

Figure 1C:
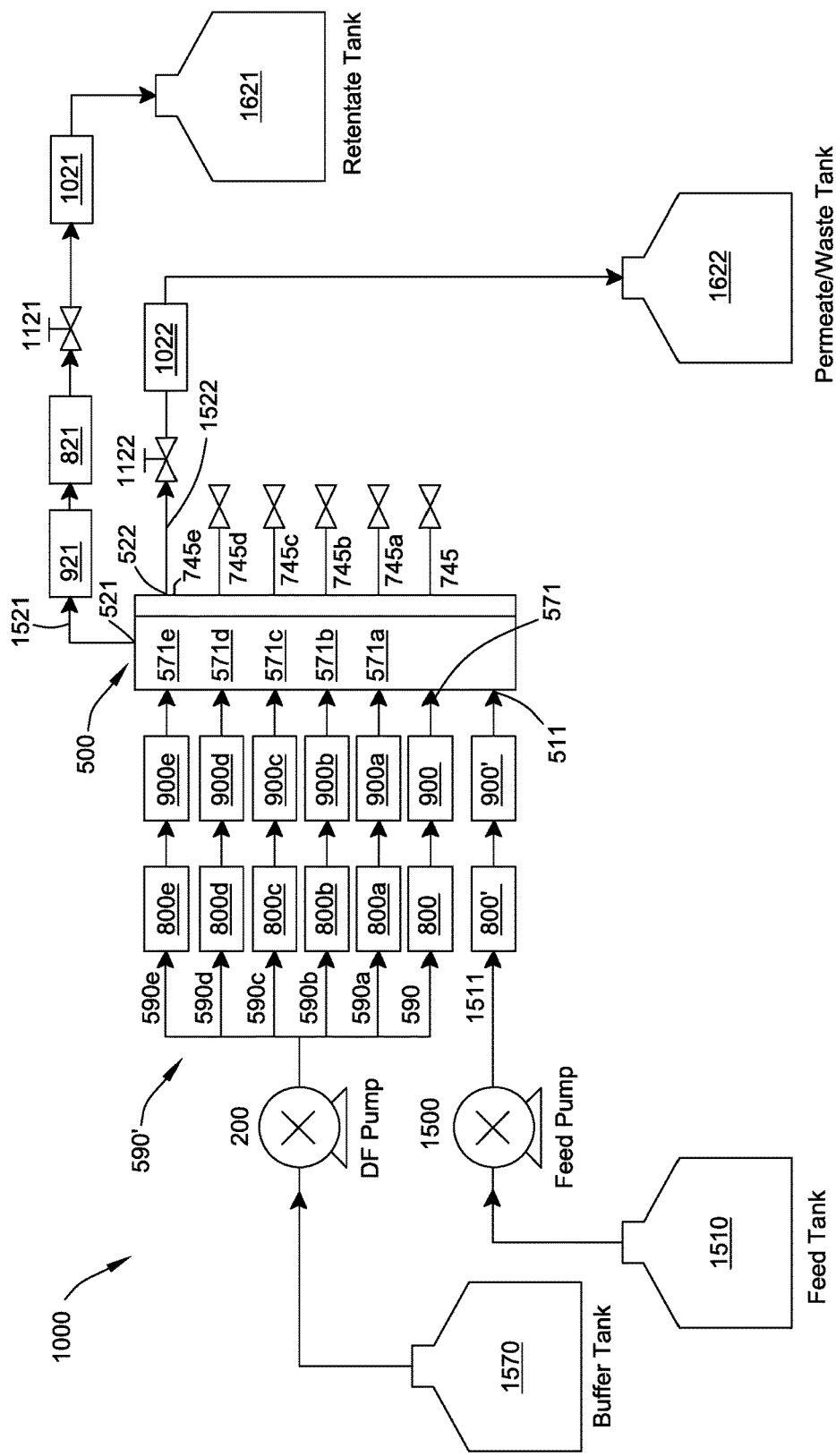
FIG. 1C is a schematic view of an embodiment of a diafiltration system according to the present invention, wherein the illustrated diafiltration system comprises a fluid treatment assembly including a plurality of fluid treatment modules, a plurality of diafiltration fluid conduits, and a diafiltration pump including a plurality of multiple channel pump heads.

For example, the embodiment of the system illustrated in FIG. 1C comprises a flow meter 800' and 900' associated with feed conduit 1511, as well as flow meters 800 (800a, 800b, 800c, 800d, 800e) and pressure sensors 900 (900a, 900b, 900c, 900d, 900e) associated with the respective diafiltration feed fluid conduits 590 (590, 590a, 590b, 590c, 590d, 590e), also comprising flow meter 821 and pressure sensor 921 associated with retentate conduit 1521, as well as conductivity sensor 1021 and throttle valve 1121 associated with retentate conduit 1521, and conductivity sensor 1022 and throttle valve 1122 associated with permeate conduit 1522. In a variation of the system of the system illustrated in FIG. 1C, the throttle valve 1122 is replaced with a flow meter, and the system does not include flow meters and pressure sensors associated with the respective diafiltration feed fluid conduits.

A variety of diafiltration fluid and feed fluid pumps (preferably microprocessor controlled drive pumps) and multiple channel (e.g., 2, 4, 8, 12, 16, and 24 channel, or more channels) pump heads (including, but not limited to stackable pump heads and cartridge pump heads) are suitable for use in the invention, and suitable pumps and pump heads are commercially available (e.g., from Cole-Palmer Instrument Company (Vernon Hills, Ill.), under the names MASTERFLEX, and ISMATEC, among others). Typically, the pumps have multiple rollers, e.g., 2, 3, 4, or more rollers). Preferably, the diafiltration pump (and for some applications, the feed pump) provides a calibrated flow rate, and, if desired, a calibrated dispensing volume. In some embodiments, the multiple channel pump head is integral with the pump. In some embodiments having a plurality of pump heads, a multiple channel head can be used, along with additional pump heads that can be multiple channel and/or single channel.

Embodiments of the invention can utilize a variety of tubing sizes and/or tubing materials, and suitable sizes and materials are known to one of skill in the art.

The diafiltration distribution plate can be formed of various materials known in the art, including, for example, polymeric materials such as polypropylene.

A variety of arrangements for cross fluid treatment assemblies comprising UF membranes between feed sides (feed channels) and permeate sides (permeate channels) are suitable for use in the invention. Typically, the feed channels and permeate channels include spacer materials and/or perforate materials such as screens or meshes. The screens or meshes can have any suitable size openings, e.g., fine, medium, or coarse size openings.

A cross fluid treatment assembly can have any number of membranes, feed channels, and permeate channels, including, for example, those disclosed in U.S. Pat. No. 8,980,088. FIG. 2B illustrates an exemplary cross fluid treatment assembly 550 comprising 4 UF membranes (560, 560', 560", 560'''), wherein each membrane is arranged between a permeate channel (562, 562', 562") and a feed channel (561, 561'). If desired, cross fluid treatment assembly components can be combined to provide cross fluid treatment sub-assemblies, e.g., wherein a permeate channel and a membrane are combined to form a permeate channel/membrane sub-assembly. For example, FIG. 2C shows top, middle, and bottom permeate channel/membrane sub-assemblies 550-1, 550-2, and 550-3, respectively, and a feed channel is arranged between the top and middle sub-assembly, and another feed channel is arranged between the middle sub-assembly and the bottom sub-assembly. FIG. 2C shows various seals associated with various cross fluid treatment components, illustrated as feed channel seals 561a', 561a", 561'a', 561'a", and permeate channel seals 562a', 562a".

In accordance with an embodiment of the invention, the UF membrane can be formed from any of numerous materials, including those known in the art, including, for example, a natural or synthetic polymer, including, e.g., regenerated cellulose, polyethersulfone, etc. The membrane can be supported or unsupported.

The membrane can have any suitable pore structure, e.g., a wide range of molecular cutoffs (such as, e.g., 10 kDa, 30 kDa, etc.) or removal ratings. Suitable membranes include those known in the art.

Further, the membrane may have, or may be modified to have, any of a myriad of fluid treatment characteristics. For example, the membrane may have a positive, negative, or neutral electrical charge; it may be liquiphobic or liquiphilic, including hydrophobic or hydrophilic or oleophobic or oleophilic; and/or it may have attached functional groups, such as ligands or any other reactive moiety, that can chemically bind to substances in the fluid. The membrane may be formed from, impregnated with, or otherwise contain a variety of materials that function to further treat the fluid in any of numerous ways. These functional materials may include, for example, sorbents, ion exchange resins, chromatography media, enzymes, reactants, or catalysts of all types that may chemically and/or physically bind, react with, catalyze, deliver, or otherwise affect substances in the fluid or the fluid itself.

The membrane can have any desired critical wetting surface tension (CWST, as defined in, for example, U.S. Pat. No. 4,925,572). The CWST can be selected as is known in the art, e.g., as additionally disclosed in, for example, U.S. Pat. Nos. 5,152,905, 5,443,743, 5,472,621, and 6,074,869.

The following examples, that are all operated in a co-current manner (FIGS. 2D and 4C show fluid flow pathways through the assemblies when operated in a co-current manner), further illustrate the invention but, of course, should not be construed as in any way limiting its scope.

The examples show that flow rate distribution through the fluid treatment assemblies is generally uniform, and manageable through a single point of control, while providing a desired level of removal efficiency.

Example 1

This example demonstrates achieving 99% (2-log; NDV=7) removal of impurities from feed streams having two different feed fluid flow rates (10 mL/min and 20 mL/min), with controlled diafiltration fluid flow rates (in each channel), in accordance with embodiments of the invention.

A diafiltration system is set up including a fluid treatment assembly as generally shown in FIG. 4 (A and B), wherein the diafiltration pump and diafiltration system are arranged as generally shown in FIGS. 1A and 1C, including a MASTERFLEX L/S Precision Variable Speed Pump Drive (Model No: EW-07528-30), with three MASTERFLEX L/S Multi-channel Pump Heads (Model No: 07536-002) and MASTERFLEX L/S High Performance Precision 2-stop tubing sets (L/S 15, 06421-15) (Cole-Palmer Instrument Company, Vernon Hills, Ill.).

The fluid treatment assembly has 6 stages, each stage having 2-in-series cross fluid treatment assemblies, each cross fluid treatment assembly including Delta regenerated cellulose UF membranes, each with a 30 kDa cutoff and a surface area of 186 cm$^2$ (total membrane area for the fluid treatment assembly is 2232 cm$^2$).

The feed solution is 10 g/L polyclonal bovine IgG in 0.025 M sodium acetate plus 0.5 M sodium chloride (NaCl) (conductivity 47 mS/cm). The diafiltration (DF) solution (buffer solution) is 0.025 M sodium acetate plus 0.05 M NaCl (conductivity 6.7 mS/cm).

When the feed fluid flow rate is 10 mL/min, the diafiltration fluid flow rate in each channel is about 11.7 mL/min, and when the feed fluid flow rate is 20 mL/min, the diafiltration fluid flow rate in each channel is about 23.3 mL/min.

An approximate 1:1 ratio is maintained between the feed flow rate and the retentate flow rate by using retentate throttling.

The results are as follows:

For fluid flow rates of 10 mL/min, the flow rate distribution per DF stage remains generally uniform around 10 mL/min. The distribution of pressures remain generally uniform around 12 psig for DF stages 1-3, decreasing toward the retentate outlet from about 9 psig to about 4 psig for DF stages 4-6.

For fluid flow rates of 20 mL/min, the flow rate distribution per DF stage remains generally uniform around 18-20 mL/min. The distribution of pressures remain generally uniform around 28 psig for DF stages 1-3, decreasing toward the retentate outlet from about 25 psig to about 9 psig for DF stages 4-6.

Example 2

This example demonstrates achieving 99.9% (3-log; NDV=13) removal of impurities from feed streams having two different feed fluid flow rates (5 mL/min and 10 mL/min), with controlled diafiltration fluid flow rates (in each channel), in accordance with embodiments of the invention.

The diafiltration system, fluid treatment assembly, and feed and DF solutions are as described in Example 1.

When the feed fluid flow rate is 5 mL/min, the diafiltration fluid flow rate in each channel is about 10.8 mL/min, and when the feed fluid flow rate is 10 mL/min, the diafiltration fluid flow rate in each channel is about 22.7 mL/min.

An approximate 1:1 ratio is maintained between the feed flow rate and the retentate flow rate by using retentate throttling.

The results are as follows:

For feed fluid flow rates of 5 mL/min, the flow rate distribution per DF stage remains generally uniform around 10 mL/min for DF stages 1-6. The pressures at DF stages 1 and 2 are 15 psig and 17 psig, respectively, the distribution of pressures remain generally uniform around 20 psig for DF stages 3-5, and decrease to about 15 psig for DF stage 6.

For feed fluid flow rates of 10 mL/min, the flow rate distribution per DF stage is in the range of around 11-9 mL/min for DF stages 2-4, and around 7 psig for DF stages 5 and 6. The distribution of pressures ranges from around 34 psig for DF stage 1, decreasing about 1 to 2 psig per stage toward the retentate outlet to about 25 psig for DF stage 6.

With respect to the feed flow rate of 5 mL/min in particular, both the pressure and flow rate management is relatively easy and uniform for targeting the 99.9% removal efficiency.

Example 3

This example demonstrates achieving 99.99% (4-log; NDV=22) removal of impurities from feed streams having a fluid flow rate 5 mL/min, with controlled diafiltration fluid flow rates (in each channel) of about 18.3 mL/min, in accordance with an embodiment of the invention.

The diafiltration system, fluid treatment assembly, and feed and DF solutions are as described in Example 1.

An approximate 1:1 ratio is maintained between the feed flow rate and the retentate flow rate by using retentate throttling.

The results are as follows:

The flow rate distribution per DF stage remains in the range of around 8-12 mL/min for DF stages 1-6. The distribution of pressures ranges from around 34 psig for DF stage 1, decreasing about 1 to 2 psig per stage toward the retentate outlet to about 26 psig for DF stage 6.

Example 4

This example demonstrates achieving 99.0% (2-log; NDV=7) removal of impurities from feed streams having feed fluid flow rates of 10 mL/min, and achieving 99.9% (3-log; NDV=13) removal of impurities from feed streams having feed fluid flow rates of 6 mL/min, with controlled diafiltration fluid flow rates (in each channel), in accordance with embodiments of the invention.

A diafiltration system is set up including a fluid treatment assembly as generally described in Example 1.

The fluid treatment assembly has 6 stages, each stage having 3-in-series cross fluid treatment assemblies, each cross fluid treatment assembly including Delta regenerated cellulose UF membranes, each with a 30 kDa cutoff and a surface area of 186 cm$^2$.

The feed solution is 60 g/L polyclonal bovine IgG in 0.025 M sodium acetate plus 0.5 M sodium chloride (NaCl) (conductivity 47 mS/cm). The diafiltration (DF) solution (buffer solution) is 0.025 M sodium acetate plus 0.05 M NaCl (conductivity 6.7 mS/cm).

When the feed fluid flow rate is 10 mL/min, the diafiltration fluid flow rate in each channel is about 11.7 mL/min, and when the feed fluid flow rate is 6 mL/min, the diafiltration fluid flow rate in each channel is about 13 mL/min.

An approximate 1:1 ratio is maintained between the feed flow rate and the retentate flow rate by using retentate throttling.

The results are as follows:

For feed fluid flow rates of 10 mL/min, the flow rate at DF stage 1 is about 6 mL/min, at DF stage 2 is about 7 mL/min, remaining uniform at about 10 mL/min for DF stages 3-6. The pressures at DF stages 1-6 are 33 psig, 31 psig, 28 psig, 16 psig, 11 psig, and 8 psig, respectively.

For feed fluid flow rates of 6 mL/min, the flow rate at DF stage 1 is 4 mL/min, at DF stage 2 is about 8 mL/min, remaining uniform at about 10 mL/min for DF stages 3-5, and about 12 mL/min for DF stage 6. The pressures at DF stages 1-6 are 29 psig, 28 psig, 24 psig, 15 psig, 10 psig, and 8 psig, respectively.

Both the pressure and flow rate management is successful and robust for the various target removal efficiencies and feed flow rates.

Example 5

This example illustrates testing utilizing diafiltration markers for better quantification of target percent removal efficiencies.

The fluid treatment assembly is as described in Example 4.

The feed solution is 60 g/L polyclonal bovine IgG with glucose as a representative small molecule. The feed solution is 60 g/L IgG in 0.025 M Na Acetate plus 0.05 M NaCl plus 50 g/L glucose (conductivity 6.7 mS/cm). The DF solution (buffer solution) is 0.025 M Na Acetate plus 0.05 M NaCl (conductivity 6.7 mS/cm).

The results are as follows: 99.9% (3-log; NDV=13) removal of glucose molecule as the small impurity having feed fluid flow rate of 5 mL/min, with controlled diafiltration fluid flow rates (in each channel). The detection limit of the glucose is 0.03 g/L.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A diafiltration system comprising
   (a) a fluid treatment assembly comprising two or more fluid treatment modules, the fluid treatment assembly comprising a feed inlet, a permeate outlet, and a retentate outlet;
   (i) each fluid treatment module comprising a cross flow treatment assembly including at least one ultrafiltration membrane, the cross flow treatment assembly having at least one feed side and at least one opposite permeate side, and a diafiltration fluid distribution plate comprising a diafiltration fluid feed inlet and a common feed permeate/diafiltration fluid permeate outlet port;

(b) two or more separate diafiltration fluid conduits, each separate diafiltration fluid conduit in fluid communication with a respective single diafiltration fluid feed inlet;

($c^1$) a feed fluid pump and a feed fluid conduit, wherein the feed fluid conduit is in fluid communication with the fluid treatment assembly feed inlet, wherein the feed fluid pump provides a controlled feed fluid flow rate through the feed fluid conduit to the fluid treatment assembly feed inlet and, ($c^2$) a diafiltration fluid pump, the diafiltration fluid pump comprising at least a first multiple channel pump head having at least two channels including separate channels for separate diafiltration fluid conduits in fluid communication with respective single diafiltration fluid feed inlets, wherein the diafiltration pump provides simultaneously controlled diafiltration fluid flow rates through each of the separate diafiltration fluid conduits to the respective single diafiltration fluid feed inlets, wherein the system is arranged to pass feed fluid through the feed inlet at a controlled flow rate that is at least about 10% less than the simultaneously controlled diafiltration fluid flow rates through each of the separate diafiltration fluid conduits.

2. The diafiltration system of claim 1, including at least one additional channel pump head having including a separate channel for a separate diafiltration fluid conduit in fluid communication with a single diafiltration fluid feed inlet, wherein the pump, via the first multiple channel pump head and the additional channel pump head, provides simultaneously controlled diafiltration fluid flow rates through each of the separate diafiltration fluid conduits to the respective single diafiltration fluid feed inlets.

3. The diafiltration system of claim 2, including at least one additional multiple channel pump head having at least two channels including a separate channel for a separate diafiltration fluid conduit in fluid communication with a single diafiltration fluid feed inlet, wherein the pump, via the first multiple channel pump head and the additional multiple channel pump head, provides simultaneously controlled diafiltration fluid flow rates through each of the separate diafiltration fluid conduits to the respective single diafiltration fluid feed inlets.

4. The diafiltration system of claim 1, including at least one additional multiple channel pump head having at least two channels including a separate channel for a separate diafiltration fluid conduit in fluid communication with a single diafiltration fluid feed inlet, wherein the pump, via the first multiple channel pump head and the additional multiple channel pump head, provides simultaneously controlled diafiltration fluid flow rates through each of the separate diafiltration fluid conduits to the respective single diafiltration fluid feed inlets.

5. The diafiltration system of claim 1, further comprising a retentate throttling valve, arranged to allow the system to maintain a desired ratio of feed flow rate to retentate flow rate.

6. A diafiltration method, the method comprising passing a feed fluid containing undesirable material and desirable biomolecules, and a diafiltration fluid suitable for washing out undesirable material from the feed fluid, through the fluid treatment assembly in the diafiltration system of claim 1, wherein the method includes (a) passing the feed fluid at a controlled feed fluid flow rate through the feed inlet of the fluid treatment assembly;

(b) passing the diafiltration fluid at a controlled diafiltration fluid flow rate through each of the separate diafiltration fluid conduits in fluid communication with respective single diafiltration fluid feed inlets, such that the diafiltration fluid washes undesirable material from the feed fluid, wherein the controlled diafiltration fluid flow rate is simultaneously controlled through each of the separate diafiltration fluid conduits;

(c) passing a feed permeate/diafiltration fluid permeate fluid through each of the common feed permeate/diafiltration fluid permeate outlet ports;

(d) passing a retentate fluid from the retentate outlet of fluid treatment assembly, the retentate fluid comprising desirable biomolecules and a lower concentration of undesirable material than the concentration of undesirable material in the feed fluid; and, (e) passing the feed permeate/diafiltration fluid permeate fluid from the permeate outlet of the fluid treatment assembly, including passing the feed fluid through the feed inlet at a controlled flow rate that is at least about 10% less than the simultaneously controlled diafiltration fluid flow rates through each of the separate diafiltration fluid conduits.

* * * * *